(12) United States Patent
Fabo et al.

(10) Patent No.: US 8,764,714 B2
(45) Date of Patent: Jul. 1, 2014

(54) DRESSING FOR PROTECTING THE SKIN AROUND OBJECTS PROJECTING OUT THEREFROM

(75) Inventors: Tomas Fabo, Molnlycke (SE); Anna Svensby, Vastra Frolunda (SE)

(73) Assignee: Mölnlycke Health Care AB, Göteborg (SE)

( * ) Notice: Subject to any disclaimer, the term of this patent is extended or adjusted under 35 U.S.C. 154(b) by 589 days.

(21) Appl. No.: 12/747,974

(22) PCT Filed: Dec. 8, 2008

(86) PCT No.: PCT/SE2008/051418
§ 371 (c)(1),
(2), (4) Date: Sep. 14, 2010

(87) PCT Pub. No.: WO2009/075636
PCT Pub. Date: Jun. 18, 2009

(65) Prior Publication Data
US 2010/0331785 A1  Dec. 30, 2010

(30) Foreign Application Priority Data
Dec. 13, 2007 (SE) ...................................... 0702792

(51) Int. Cl.
*A61M 5/32* (2006.01)

(52) U.S. Cl.
USPC ........................................................ 604/180

(58) Field of Classification Search
USPC .................................................. 604/174, 180
See application file for complete search history.

(56) References Cited

U.S. PATENT DOCUMENTS

| | | | | |
|---|---|---|---|---|
| 3,678,933 A | * | 7/1972 | Moore et al. | 604/366 |
| 3,683,911 A | * | 8/1972 | McCormick | 604/180 |
| 3,927,672 A | * | 12/1975 | Garcia | 604/180 |
| 4,221,215 A | * | 9/1980 | Mandelbaum | 604/327 |
| 4,499,896 A | | 2/1985 | Heinecke | 128/156 |
| 4,621,029 A | | 11/1986 | Kawaguchi | |
| 4,699,616 A | * | 10/1987 | Nowak et al. | 604/180 |

(Continued)

FOREIGN PATENT DOCUMENTS

| | | |
|---|---|---|
| AU | 20089336285 | 12/2008 |
| CA | 2706181 | 12/2008 |

(Continued)

OTHER PUBLICATIONS

International Search Report dated Mar. 27, 2009, from corresponding PCT application.

(Continued)

*Primary Examiner* — Emily Schmidt
(74) *Attorney, Agent, or Firm* — Ballard Spahr LLP (57) ABSTRACT

The present invention relates to a dressing (1) for protecting the skin around objects projecting out from the skin, the dressing including a first liquid impermeable film layer (2) coated with a skin friendly adhesive (3) on the lower side thereof, i.e. the side intended to adhere to the skin when the dressing is used. According to the invention a body (4) of absorbent material is enclosed between the first film layer (2) and a second liquid impermeable film layer (5), the second film layer being affixed to the first film layer in parts extending beyond the periphery of the body of absorbent material, and the dressing includes an element (8) for facilitating passing of an object projecting out from the skin through the dressing.

20 Claims, 4 Drawing Sheets

(56) References Cited

U.S. PATENT DOCUMENTS

| | | | |
|---|---|---|---|
| 4,793,337 A * | 12/1988 | Freeman et al. | 602/56 |
| 4,917,112 A | 4/1990 | Kalt | |
| 4,991,574 A | 2/1991 | Pocknell | 128/156 |
| 5,540,922 A | 7/1996 | Fabo et al. | 424/402 |
| 5,635,201 A | 6/1997 | Fabo et al. | 424/443 |
| 5,973,221 A | 10/1999 | Collyer | 602/46 |
| 6,007,562 A | 12/1999 | Harren | 606/213 |
| 6,036,721 A | 3/2000 | Harren | 606/213 |
| 6,168,800 B1 * | 1/2001 | Dobos et al. | 424/405 |
| 6,607,799 B1 | 8/2003 | Heinecke | 428/40.1 |
| 6,846,508 B1 * | 1/2005 | Colas et al. | 427/2.31 |
| 2001/0025159 A1 * | 9/2001 | Fleischer | 604/174 |
| 2004/0220505 A1 | 11/2004 | Worthley | |
| 2007/0225652 A1 * | 9/2007 | Scherr | 604/180 |
| 2008/0114278 A1 | 5/2008 | Fabo et al. | 602/48 |

FOREIGN PATENT DOCUMENTS

| | | |
|---|---|---|
| CN | 200880120337 | 12/2008 |
| DE | 297 10 855 | 10/1997 |
| DE | 20 2006 005 966 | 10/2006 |
| EP | 0300620 | 1/1989 |
| EP | 0 352 086 | 1/1990 |
| EP | 2008860047 | 12/2008 |
| GB | 2 099 306 | 12/1982 |
| JP | A58/180152 | 2/1985 |
| JP | A63-043668 | 2/1988 |
| JP | A64-034370 | 2/1989 |
| JP | A08-154964 | 12/1995 |
| JP | A10-504216 | 2/1996 |
| JP | A2001/502956 | 3/2000 |
| JP | A2002-527173 | 8/2003 |
| JP | A2006-517427 | 7/2004 |
| JP | 2010-0537895 | 12/2008 |
| KR | 10201070122179 | 12/2008 |
| SE | 0702792-3 | 12/2007 |
| WO | 03/020355 | 3/2003 |
| WO | 2004/004816 | 1/2004 |
| WO | WO 2004/060412 | 7/2004 |
| WO | 2006/075950 | 7/2006 |
| WO | 2006/099173 | 9/2006 |
| WO | 2007/011596 | 1/2007 |
| WO | 2007/013912 | 2/2007 |
| WO | WO 2007/118636 | 10/2007 |
| WO | PCT/SE2008/051418 | 12/2008 |

OTHER PUBLICATIONS

International Preliminary Report on Patentability issued Jun. 15, 2010 by the International Searching Authority for Application PCT/SE2008/051428 filed Aug. 12, 2008 (Applicant—Molnlycke Health Care AB // Inventor—Fabo, et al.) (pp. 1-8).

Written Opinion issued Mar. 27, 2009 by the International Searching Authority for Application PCT/SE2008/051428 filed Aug. 12, 2008 (Applicant—Molnlycke Health Care AB // Inventor—Fabo, et al.) (pp. 1-7).

English Translation of Office Action issued Oct. 23, 2012 for Japanese Patent Application No. 2010-537895, which was filed Dec. 8, 2008 (Inventor—Fabo; Applicant—Molnlycke Health Care AB) (pp. 1-5).

* cited by examiner

DRESSING FOR PROTECTING THE SKIN AROUND OBJECTS PROJECTING OUT THEREFROM

TECHNICAL FIELD

The present invention relates to a dressing for protecting the skin around objects projecting out from the skin, said dressing comprising a first liquid impermeable film layer coated with a skin friendly adhesive on the lower side thereof, i.e. the side intended to adhere to the skin when the dressing is used.

BACKGROUND OF THE INVENTION

Many medical or surgical interventions include penetration of objects, such as tubes, instruments and other medical articles, through the skin and into tissue or cavities in the body of a patient. In certain cases such objects are left in the body for shorter and longer periods, from a few minutes to months or years. Examples of such objects are percutaneous endoscopic gastrostomy (PEG) feeding tubes, tracheostomies, cannulae, catheters and pins for external fixation of bones. Leakage of body fluids often occurs around such penetrating objects. The leaking body fluids often gather around the penetration openings for the objects which can result in maceration of the skin, irritation of the skin, skin infection and even sores.

In order to take care of possible leaking fluid around penetration openings, compresses or pads of cotton wool or other absorbent materials are often wound or laid around the object projecting out of the skin. A slit is often made in such pads to facilitate application thereof in the area around the object. Such pads or compresses are usually affixed to the skin and to the object by self-adhesive tape. Wound dressings or plasters comprising a wound pad and a self-adhesive fixation part are also used. A drawback by such compresses or pads is that they exhibit a wet or moist surface to the skin after having absorbed fluid. Thereby there is still a risk for maceration and skin irritation. Such pads or compresses have to be changed often in order to exhibit a dry surface to the skin. Since the skin around penetration openings often is very sensitive, the frequent changing of absorbent pads or compresses increases the risk for irritation of and damage to the skin which in turn increases the risk for infection to occur.

WO 2007/013912 describes a disposable pin site wound protection system for covering the entry or exit of a surgical pin, wherein the system substantially reduces the time required to change a dressing at a pin site wound. This system comprises a sponge and a clip, both of which are designed to be attached to a pin site wound.

Allevyn Tracheostomy from Smith&Nephew is made of a non-adhesive, cushioned foam having a key-hole shaped hole for application around a tracheostomy tube or on the stoma.

Drawbacks with non-adhesive products are the weak affixing to skin which can increase the risk of leakage and in turn cause skin maceration and even infections.

WO2006/99173 relates to a fork-like device for changing tracheostomy sponges on a patient.

As tracheostomy dressings in hospitals today are often used adhesive dressings or foams cut manually to fit the stoma. Other than a risk of maceration and skin damage there is also a risk of leakage at dressing changes with such non adhesive and non encapsulated foam dressings.

The adhesives of the fixation tapes, wound dressings or plasters usually used for such products usually take portions of the skin away when these products are loosened from the skin. The risk for damage to the skin by frequent changing of such products is thus relatively high if the object projecting out of the penetration opening is disposed in the body of the patient during a long period of time. The changing of such products will also lead to pain to the patient since it hurts when the product is loosened from the skin. Another drawback is that gauzes or other types of absorbent material disposed around such objects will have a wet outside which can soil clothes or the like disposed outside the penetration opening.

Prior art describes the problem of time consuming dressing changes, but it does not describe the problem of exudate leaking out from the wound to the periwound skin causing risk of maceration and bacterial growth on the skin, which can lead to wound infection.

The objective of the invention is to improve a dressing of the kind mentioned in the introduction which is easy to apply and eliminates or at least greatly reduces the drawbacks mentioned above.

SUMMARY OF THE INVENTION

This objective is accomplished by a dressing for protecting the skin around objects projecting out from the skin, said dressing comprising a first liquid impermeable film layer coated with a skin friendly adhesive on the lower side thereof, i.e. the side intended to adhere to the skin when the dressing is used, characterised by a body of absorbent material enclosed between the first film layer and a second liquid impermeable film layer, said second film layer being affixed to the first film layer in parts extending beyond the periphery of the body of absorbent material, and by means for facilitating passing of an object projecting out from the skin through the dressing. In such a dressing, fluid leaking from the opening will be prevented from being spread out on the skin by the film adhered to the skin so as to follow substantially all irregularities thereof. Leaking fluid will therefore follow the object and be absorbed by the absorbent material which will be in contact with the leaking fluid around the periphery of the object. Since the absorbent material is covered by film on both its lower and upper side neither the skin nor the environment can come into contact with wet absorbent material. A characteristic of a skin friendly adhesive is that it can be loosened without damage to the skin so the dressing according to the invention can be changed without risk for damage to the skin or skin irritation.

In a first preferred embodiment, said means for facilitating passing of an object projecting out from the skin through the dressing includes a hole extending through the first and second film layer and the body of absorbent material disposed therebetween.

In a second preferred embodiment, said means for facilitating passing of an object projecting out from the skin through the dressing comprises at least two secondary slits starting in the middle of the dressing and being distanced from each other in a circumferential direction in relation to said starting point, each secondary slit ends before reaching an outer edge of the absorbent body.

In the first embodiment, at least two secondary slits might extend from the perimeter of the hole in the dressing, said secondary slits being distanced from each other in a circumferential direction, each secondary slit ends before reaching an outer edge of the absorbent body.

In both embodiments a primary slit can be extended through the dressing from an edge thereof towards a middle portion of the absorbent body. If not, such a slit should be cut by the person using the dressing before it is applied.

A stiffening layer is preferably releasably attached to the upper side of the dressing.

Said stiffening layer has advantageously the form of a frame surrounding a central portion of the dressing.

Grip tabs preferably extend out from said frame on both sides of said primary slit and said frame can comprise one or more portions projecting inwardly towards the middle of the absorbent body on both sides of said primary slit.

The edges of the first and second film layer along the primary slit can be attached to each other in order to ensure that only the side of the absorbent body facing the periphery of the object can be reached by leaking fluid. Said edges of the first and second film layer are preferably attached to each other by a welding seam.

Said body of absorbent material can wholly or partly be made of absorbent foam material. Furthermore, it can include fibrous material disposed in a region or regions distanced from said hole and/or said secondary slits.

Finally, said primary slit can be discontinuous in the part thereof extended outside of the absorbent body.

BRIEF DESCRIPTION OF THE DRAWINGS

The invention will now be described with reference to the enclosed figures, of which.

DESCRIPTION OF EMBODIMENTS

Figure 1:
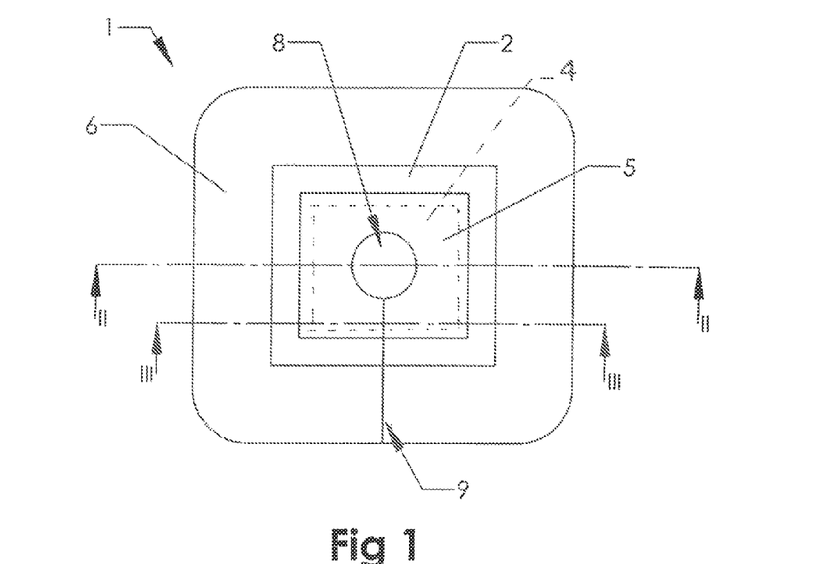
FIG. 1 schematically discloses a plan view of a dressing according to a first preferred embodiment of the invention.
Figure 2:
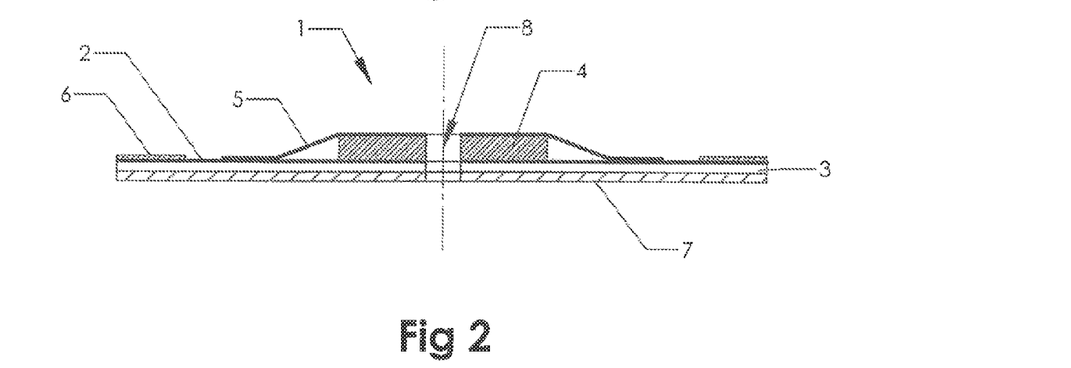
FIG. 2 shows a sectional view along line II-II in FIG. 1.
Figure 3:
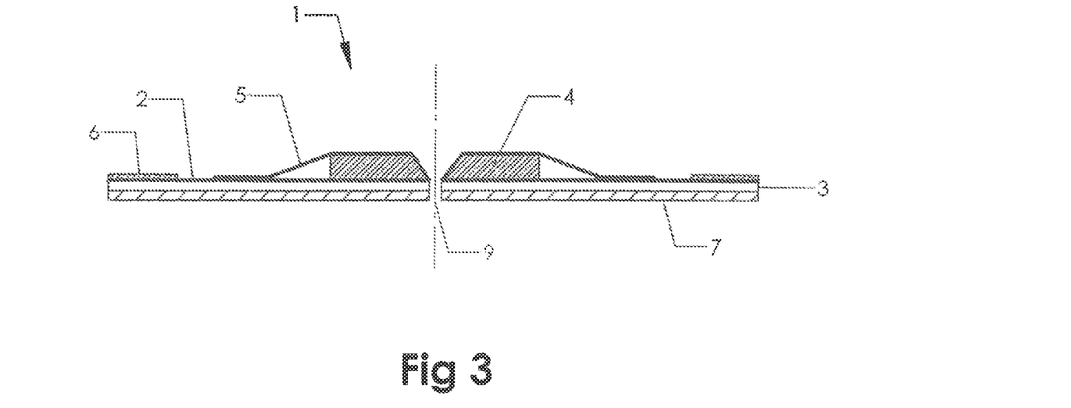
FIG. 3 shows a sectional view along line III-III in FIG. 1, FIG. 4 schematically illustrates the measurement of strength of adhesion to the skin.

In FIGS. 1-3, a first preferred embodiment of a dressing 1 according to the present invention is schematically disclosed. The dressing includes a first plastic film 2 which is coated with an adhesive layer 3 on one side thereof. On the upper side of film 2, i.e. the side opposite to the side coated with the adhesive layer 3, a body 4 of absorbent material is disposed in a middle region of the dressing. Said body 4 of absorbent material is covered by a second plastic film 5 which extends beyond the circumference of the body 4 and is affixed to the first film 2 in the parts thereof extending outside of the body 4 by any suitable means, such as a glue or weld seam. The body 4 of absorbent material can be attached to one or both of the films 2 and 5 but can also be left unattached thereto.

A frame 6 of stiffening material is releasably attached to the first film 2 on the upper side thereof in order to facilitate handling and application of the dressing. This frame is taken away during the application of the dressing. The dressing 1 is also provided with a release layer 7 which protects the adhesive layer during storing and transport of the dressing and is taken away before application of the dressing.

A hole 8 going through all of the layers in the dressing is present in the middle part of the dressing 1. A through-going slit 9 extending from an edge of the dressing to the periphery of said hole 8 is also present in the embodiment shown in FIGS. 1-3. In the shown embodiment, the films 2 and 5 are affixed to each other along the edges of the slit 9, for example by a weld seam.

The dressing 1 according to the present invention is used for protecting the skin around openings in skin for the penetration of objects, such as tubes, instruments and other medical articles. Such objects penetrate through the skin and into tissue or cavities in the body of a patient as a result of from many medical or surgical interventions, and are in certain cases left in the body for shorter and longer periods. Examples of such objects are PEG tubes, tracheostomies, tubes, cannulae, catheters and pins for external fixation of bones.

When applying the dressing 1 around an opening in the skin out of which an object projects, the slit 9 is opened so that the hole 8 can be arranged surrounding the object, such as a tube. The release layer is first removed before the slit 9 is opened and one of the parts of the dressing to the right or the left of the slit 9 and the prolonging thereof is attached to the skin with the periphery of the right or left part of hole 8 coinciding with the periphery of the opening in the skin. Thereafter, the other part of the dressing, to the left or right of slit 9, is attached to the skin so that the edges of the slit 9 abut each other. The stiffening layer is then removed from the applied dressing.

The plastic films 2 and 5 are preferably of polyurethane and have a thickness of 5-100 μm, preferably 10-50 μm. Films of other plastic materials such as polyethylene, polypropylene or polyester could also be used.

The material in the body 4 is wholly or partly foam, for example polyurethane foam. However, fibrous absorbent materials, such as wadding, felt, nonwoven, textiles, can be used in the present invention. Preferably, absorbent fibres, such as cotton or viscose fibres or fibres that swell and form a gel are then used, for example carboxymethylcellulose, alginates or the like. Particulates of so called superabsorbents can be added to the body, preferably mixed together with fibrous materials. In order to prevent superabsorbent particles from migrating out of the body 4, such particles are not present in the middle part of the body which surrounds the opening in the skin when the dressing 1 is applied. Moreover, if superabsorbent particles are present in the absorbent body 4, it is highly preferred that the films 2 and 5 are sealed to each other along the edges of slit 9. If films 2 and 5 are not sealed to each other along the edges of the slit 9, no superabsorbent particles should be present in regions running along the slit 9. It is possible to use foam material in the middle part of the body and in regions along the edges of the slit 9 and fibrous material with superabsorbent particles mixed therein in other parts of the absorbent body.

A principal function of the adhesive coating 3 is to attach the dressing 1 tightly to the skin of the patient, so that the fluid-borne transport of bacteria between the skin and the adhesive coating is prevented, and to attach the dressing securely to the skin, so that the product remains in place during all the normal loadings to which dressings are subjected.

The adhesive in the coating must also be skin friendly and must permit removal of the film dressings without causing damage to the skin or pain to the patient. This requirement presents a major problem in the case of those types of pressure-sensitive adhesives that are currently used as adhesive coatings for film dressings. Such adhesives often attach themselves to the skin so strongly that parts of the Stratum Corneum, that is to say the uppermost layer of the skin, become stuck to the adhesive and are pulled away from the skin when the film dressing is loosened. This can lead to irritation of and damage to the skin.

An example of a skin friendly adhesive that can fulfil these requirements is silicone gel. Silicone gel is very soft and possesses low surface energy, and it adapts very well to the skin, that is to say it flows out into any unevennesses in the skin and creates a large contact surface between the skin and the silicone gel. This large contact surface helps the silicone gel to become attached securely to the skin, in spite of the fact that the strength of the adhesive attachment of the silicone gel to the skin is not in itself so strong. The adhesive strength constitutes a measure of the energy required in order to separate/pull off the adhesive layer from the skin. A contributory factor to the fact that high energy, and thus a high pulling force, is required in order to remove the silicone gel from the skin, in spite of the relatively weak strength of the adhesive attachment, is that a lot of energy is consumed in stretching the soft silicone gel before it releases from the skin. The softer and thicker the layer of silicone gel, the greater the force/energy required to remove the gel from the skin.

The use of a harder adhesive will require a higher strength of adhesive attachment in order for the pulling force to be as high as for a softer adhesive. A strong adhesive attachment between the skin and the adhesive can easily lead to skin cells being pulled from the skin in conjunction with the removal of the adhesive.

Suitable soft, skin friendly adhesives for the adhesive layer 3 are for example addition curing RTV (Room Temperature Vulcanizing) silicone systems which after mixing crosslink and form a self-adhering gel. Examples of such RTV silicone systems are given in EP 0 300 620 A1 describing so called "gel forming compositions" constituted of a alkenylsubstituted polyorganosiloxane containing hydrogen atoms bonded to some of the silicon atoms and a platinum catalysator.

Wacker SilGel 612 is a commercially available RTV-silicone system. It is a two component system. By varying the proportions between the two components A:B from 1.0:0.7 to 1.0:1.3 the softness and adhesion level of the formed material can be varied.

Examples of further soft, skin friendly silicone gels that can be used are NuSil MED-6340, NuSil MED3-6300, NuSil MED12-6300 from NuSil Technology, Carpintiera, Ga., USA and Dow Corning 7-9800 from Dow Corning Corporation, Midland, USA.

Also other soft, skin friendly adhesives might be used in the present invention, for example hot-melts similar to Dispomelt® 70-4647 from National Starch and Chemical Company, Bridgewater, N.J., USA.

Because the characteristics of the skin vary from person to person, the adhesive capacity of the adhesive coating to the skin naturally also varies for different patients. The adhesive strength is also dependent on the thickness of the soft adhesive and the mechanical characteristics of the barrier layer. The standard methods for the measurement of adhesion that are available today use plates of various kinds, for example made of steel or glass, and they do not produce values that are relevant for the measurement of the adhesion to the skin. The values for the strength of the adhesive attachment of an adhesive to the skin, as indicated below, must be measured by means of a method of the kind illustrated schematically in FIG. 4 and developed by the applicants.

Figure 4:
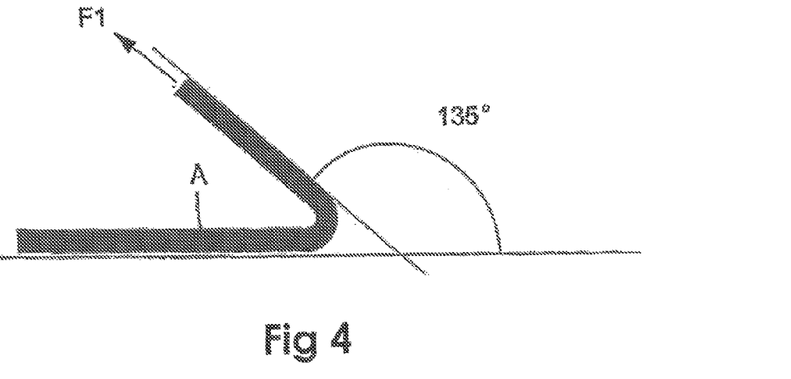

Strips of a self-adhesive dressing, for which the strength of the adhesive attachment to the skin is to be measured, are punched out with dimensions of 25×125 mm. It should be noted that all the strips are also provided with a carrier layer on the rear side of the film dressing. (The function of this carrier layer is to stiffen up the strips when they are applied to the skin). The strips are then applied to the skin on the back of healthy volunteers. The strips are carefully smoothed into place with a finger, and the carrier layer on the rear side of the strips is then removed. Finally, the strips are pressed securely against the skin for 3 seconds with the help of a sponge made of foam plastic (42×182 mm, thickness=48 mm) glued securely to a steel sheet (50×200 mm, thickness=1 mm). The applied pressure is estimated to 6 kN/m$^2$. The strips are left in place on the skin for 2 minutes. The strips are then pulled off at a rate of 25 mm/sec, and the removal force F1 is measured. The angle of removal, that is to say the obtuse angle that is formed between the surface of the skin and the removed part of the strip, must be 135°. The strength of the adhesive attachment of the strip to the skin is constituted by the mean value of the force F1.

Adhesives that are suitable for use in film dressings in accordance with the invention must exhibit a strength of adhesive attachment of at least 0.2 N/25 mm in accordance with this method. The strength of adhesive attachment is preferably 1-2.5 N/25 mm.

Figure 5:
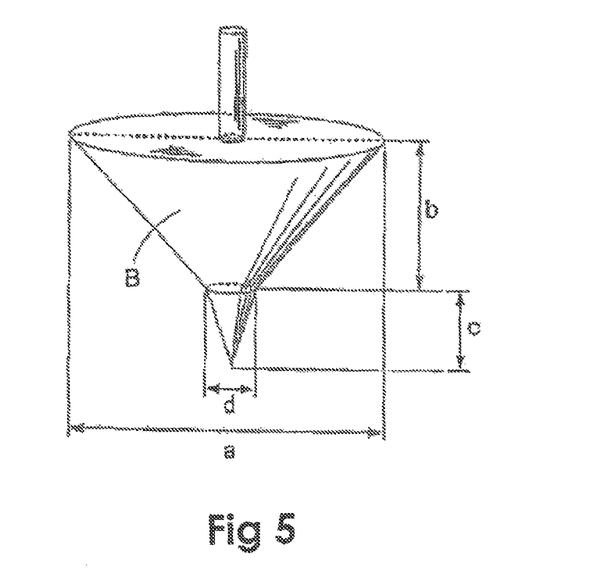
FIG. 5 shows a cone used for softness measurement.
Figure 6:
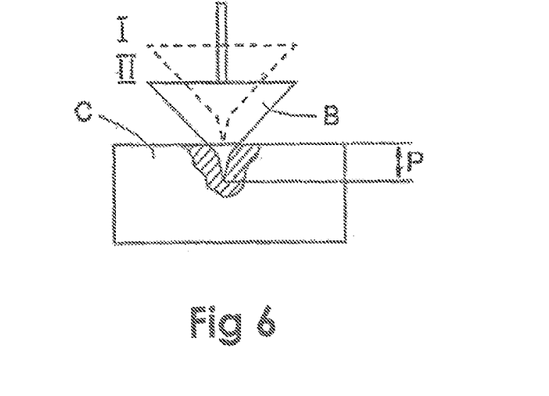
FIG. 6 illustrates a method of measuring softness.

Adhesives in accordance with the present invention must exhibit a softness that exceeds 10 mm measured by means of a method based on ASTM D 937 and ASTM D 51580. Certain deviations, as can be appreciated below, have been made. FIGS. 5 and 6 illustrate this modified method of measuring the softness of an adhesive by causing a cone B with a weight of 62.5 g to penetrate down by the effect of gravity into a 30 mm thick test piece C of the adhesive for which the softness is to be determined. The test piece is obtained by filling a cylindrical glass container having an internal diameter of 60 mm and an internal height of 35-40 mm, with adhesive to a depth of 30 mm. In the case of a silicone gel, it is necessary to fill a non-cured silicone prepolymer into the container, and then to cross-link it to a gel in the glass cylinder. The cone used is illustrated in FIG. 5 and has the following dimensions: a=65 mm, b=30 mm, c=15 mm and d=8.5 mm. In the performance of the method for measurement of the softness, the cone B is first lowered down into a position I, as illustrated with broken lines in FIG. 6, and in which the tip of the cone just touches the surface of the test piece C. The cone B is then released, so that it is able to penetrate down into the test piece C by the effect of gravity. The number of millimeters by which the tip B of the cone has penetrated into the test piece C after 5 seconds is measured and constitutes the penetration value P, the value of which is greater in proportion to the softness of the test piece. The penetration value P represents the softness index used in the present invention. A PNR 10 penetrometer supplied by Sommer & Runge KG, Germany is used in the performance of the method.

It has also been found that the risk for leakage due to irregularities in the skin will be less the softer the adhesive and the higher the basis weight. It is therefore preferred that the softness of the adhesive is greater than 10 mm and the basis weight is at least 50 g/m$^2$.

In order to ensure that only a low application force is required in conjunction with the application of film dressings in accordance with the present invention, it is recommended that the softness of the soft, skin friendly adhesive that is used should be greater than 10 mm, and that it should preferably lie between 12 and 17 mm. The softer an adhesive, the more rapidly it will flow into any unevennesses in the substrate, which means that the dressings including such adhesives are leakproof immediately after their application to normal skin. At a softness value greater than 17 mm, there is a risk of the inner cohesion of the adhesive being too low, so that residues of adhesive are left behind on the skin in conjunction with the removal of an applied dressing.

Furthermore, no hairs are pulled out when removing film dressings provided with soft, skin friendly adhesive.

The products proposed in the present invention are normally supplied packed in sterile conditions, which means that the adhesives used must be capable of being sterilized, as must other components of such articles, of course.

The stiffening frame 6 is preferably made of silicone coated paper. It is also possible to use polyethylene coated paper or other stiffening material, such as plastic film of a suitable thickness. Examples of plastic materials which can be used for the stiffening frame 6 are polyethylene, polypropylene, polyester, polystyrene, and dimethylsiloxane.

The release layer 7 is preferably constituted by a plastic film, for example of polyethylene, having protrusions on the side thereof facing the adhesive layer 3.

The first film 2 might have small perforation in the part thereof being located under the absorbent body 4. Such perforations enable the absorbent body to absorb possible moisture on the skin. However, there are preferably no such perforations in the immediate vicinity of the hole 8. Furthermore, such perforations might be formed so that they promote fluid flow in one direction only, namely the direction towards the absorbent body.

Since the absorbent body is an integral part thereof, the dressing 1 is easy to apply around an opening in the skin. Furthermore, by having a skin friendly adhesive coated on a thin plastic film, the adhesive layer and the film can follow the irregularities of the skin thereby ensuring a fluidtight area around a penetration opening. This ensures that possible fluid leaking out of the penetration opening will have to follow the peripheral surface of the object projecting out of the opening. Leaking fluid will therefore come in contact with the absorbent body and be absorbed by this body. Since this body is enclosed between the plastic films no wet surface is exhibited against the skin or the environment. Thereby the risk for infections and soiling of the environment is eliminated if the dressing is changed before it is wholly saturated. Since a skin friendly adhesive is used no stripping of or damage to the skin is caused by such a change of dressing.

The dressing shown in FIGS. 1-3 thus eliminates all drawbacks of prior art discussed in the introductory part of the present description.

In FIGS. 7-13 further embodiments of dressings according to the present invention are shown in plan views. They are all composed of components essentially similar to the components of the dressing shown in FIGS. 1-3 and the dressings and components of the embodiments according to FIGS. 4-10 are given the same reference numerals with the addition 10, 100, 200, 300, 400, 500, and 600, respectively.

Figure 7:
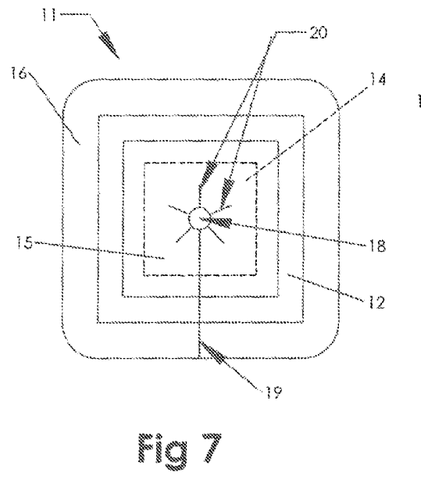
FIGS. 7-13 show plan views of dressings according to further embodiments of the invention.

The dressing 11 according to the embodiment shown in FIG. 7 differs from the dressing shown in FIGS. 1-3 by having secondary slits 20 radially extending from the hole 18 in addition to the primary slit 19. In the shown example there are five secondary slits 20 together with primary slit 19 evenly distributed around the periphery of hole 18. The advantage by such a construction of the dressing is that the dressing 11 can be accommodated around projecting objects of different sizes and having different cross-sections. The secondary slits 20 do not reach the outer edge of the absorbent body but end before reaching said edge. More than or less than five secondary slits can be arranged around the hole 18 but preferably at least two secondary slits will be made.

It is of course possible to let the secondary slits be cut by the user before use and thus only have a hole 18 and no secondary slits. In order to facilitate cutting of secondary slits by the aid of scissors, the diameter of hole 18 should then be at least 5 mm.

Figure 8:
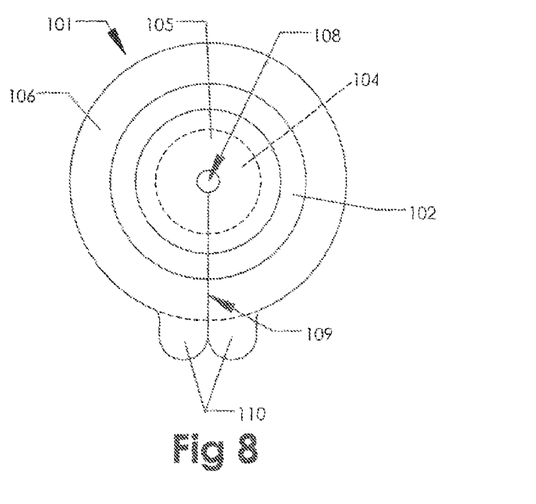

In FIG. 8, the dressing 101 has a circular shape and also the absorbent body 104 and the second film layer 105 is circular. A further difference from the dressing 1 according to the embodiment described with reference to FIGS. 1-3 is that the stiffening layer 106 is provided with grip tabs 110 projecting out from the edge of film layer 102 and extending along the slit 109. Preferably similar grip tabs with the same horizontal extension as the tabs 110 are provided in the release layer.

Figure 9:
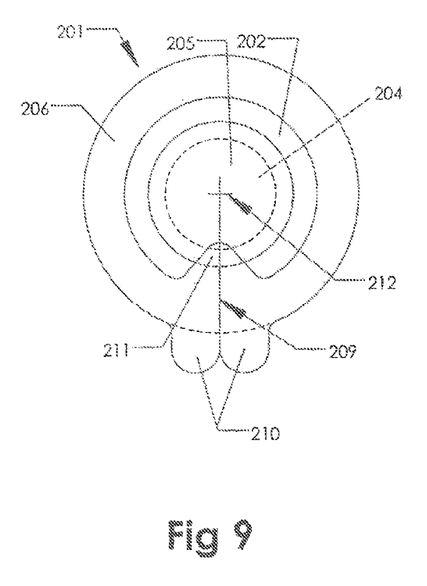

In FIG. 9, the dressing 201 has a circular shape and is provided with grip tabs 210 as the dressing according to the dressing described with reference to FIG. 8. Furthermore, there is no hole in the middle of the dressing but a slit 212 crosses the slit 209 a distance from the inner end thereof. Although the slit 212 in the shown embodiment runs perpendicular to slit 209, this is not necessary but the slit 212 can forms other angles to the slit 209. It is to be noted that in analogy with the embodiment according to FIG. 7 the part of slit 209 extended from the edge of the dressing to the crossing point for slits 209 and 212 is defined as a primary slit whereas the parts of slits 209 and 212 radially extending outwardly from the crossing point is defined as secondary slits. Another difference from the dressings 1,11,101 of FIGS. 1-3, 7 and 8, respectively is that the stiffening layer 206 is provided with an inwardly projecting portion 211 extending on both sides of the primary slit 209 towards the middle of the absorbent body but ending before reaching the middle of the absorbent body. The projecting portion 211 will make it easier to open up the slit 209 in order to apply the dressing around an object projecting out from the skin.

Figure 10:
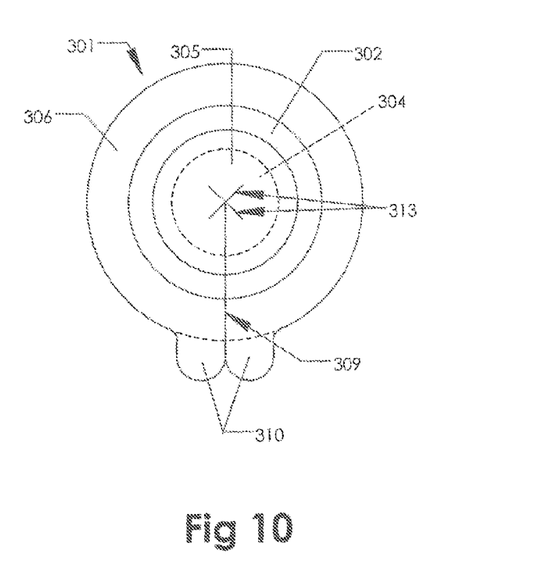

In FIG. 10 a dressing 301 according to a further embodiment is shown. This dressing 301 differs from dressing 201 shown in FIG. 9 in that a portion projecting from the inner periphery of the stiffening layer is lacking and that instead of one secondary slit crossing the slit 309, two slits 313 are crossing slit 309. It is to be noted that in accordance with the definition above five secondary slits are thereby created. Also in this embodiment the number of secondary slits can be varied.

Figure 11:
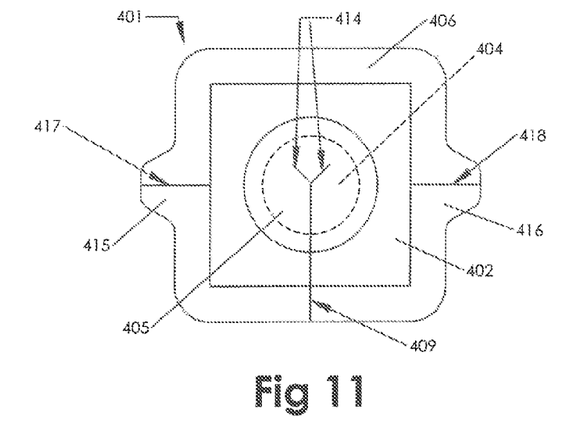

In FIG. 11 a dressing 401 having a generally rectangular shape is shown. The absorbent body 404 and the secondary film layer 405 are however circular. The slit 409 ends in the middle of the absorbent body 404 and constitutes thereby a primary slit. Two secondary slits 414 extend from the end of the primary slit 409 forming a Y together with the primary slit 409. Two grip tabs 415 and 416 extend outwardly from the edges of the stiffening layer 406 parallel to the primary slit 409. Each of the tabs 415,416 are divided into two tabs by slits 417, 418 in the stiffening layer 406. Prolongations of the two slits 417,418 in the stiffening layer 406 do not meet each other.

Figure 12:
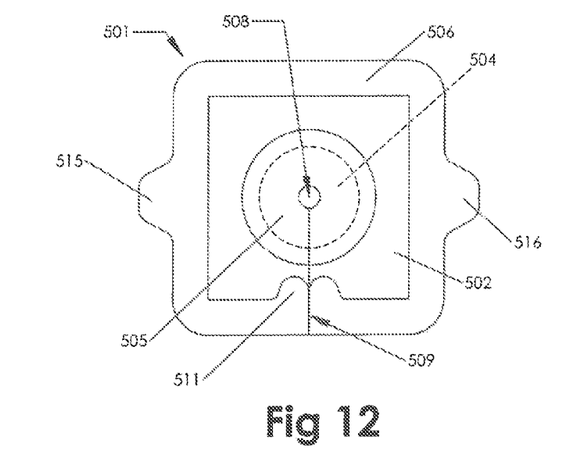

In FIG. 12 a dressing 501 is shown. This dressing differs from the dressing shown in FIG. 11 in that a hole 508 is made in the middle of the dressing instead of the secondary slits 414 according to the dressing of FIG. 11. Furthermore, the tabs 515,516 are not divided into two parts by slits in the stiffening layer 506. Finally, the stiffening layer 506 is provided with an inwardly projecting portion 511 extending on both sides of the primary slit 509 towards the middle of the absorbent body but ending before reaching the middle of the absorbent body which portion is similar to the projecting portion 211 in the dressing of FIG. 9.

Figure 13:
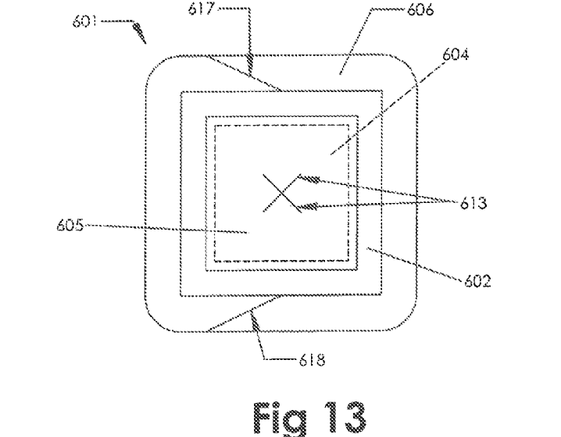

In FIG. 13, a dressing 601 which differs from the dressing according to FIGS. 1-3 mainly in that it lacks a primary slit, is shown. However, it is clear that a primary slit should be present in the dressing before use so it is intended that the user will cut a primary slit into the dressing 601 before use. The dressing 601 neither have a hole in the middle thereof but have instead secondary slits 613 similar to the slits 313 in the dressing according to FIG. 10. Furthermore, slits 617 and 618 are provided in the stiffening layer 606.

The absence of a primary slit in a dressing according to invention during storing and transport can be considered to be advantageous by certain users. It is therefore envisaged that all of the shown and discussed embodiments of a dressing according to the invention can lack a primary slit after manufacture and thus before use.

The dressings according to the present invention prevent exudate from openings in the skin from leaking out on the skin around such an opening by forcing the exudate into an absorbent body which is incorporated between two liquid impermeable films, where the bottom film facing the skin is coated with a skin friendly adhesive. Thus, the exudate is locked up in the absorbent body reducing the risk of causing skin break down and bacterial growth on the skin. Thanks to the backing film, on top of the absorbent body, this dressing also reduces the risk of soiling cloths or bedclothes.

The dressings according to the present invention are also ready-to-use dressings for e.g. tracheostomy. The dressing has a skin-friendly adhesive coating and an optimized distribution pattern of absorbent materials, which makes it adhere tightly to the stoma-surrounding skin without giving rise to leakage, and provides good fluid-retention capacity. In addition, the dressing is an all-in-one solution, which is easy to apply and remove and thereby time-saving and further alleviates the need of specific applicator devices.

The herein presented dressing is of course not limited to tracheostomy use and can accordingly be applied in other skin penetrating medical areas, such as together with pins in orthopedics or for affixing and avoid leakages with percutaneous endoscopic gastrostomy (PEG) feeding tubes.

The described embodiments can of course be modified in several ways without leaving the scope of invention. Thus can all the different features of the different embodiments be mixed, for example can the holes in certain embodiments be substituted by the secondary slits of other embodiments. The shapes of the dressings and the components thereof can also be varied. A way of satisfy possible demands for ease of handling before use would be to make the primary slit be discontinuous in its portion extending outside the absorbent body, for example by forming a perforation line in this region. This feature can of course be present in all embodiments in which a primary slit is present. Furthermore, the second film layer can have the same extension as the first film layer. The scope of protection shall therefore only be restricted by the content of the enclosed patent claims.

The invention claimed is:

1. A dressing for protecting the skin around an object projecting out from the skin, the dressing comprising a first liquid impermeable film layer coated with a soft adhesive on the side intended to adhere to the skin when the dressing is used, wherein the soft adhesive exhibits a softness that exceeds 10 mm, wherein a body of absorbent material is enclosed between the first film layer and a second liquid impermeable film layer, the second film layer being affixed to the first film layer in parts extending beyond the periphery of the body of absorbent material, and wherein means are provided for facilitating passing of an object projecting out from the skin through the dressing, wherein the means provided for facilitating passing of an object projecting out from the skin through the dressing has a periphery, and wherein at least a portion of the soft adhesive adjacent to the periphery of the means provided for facilitating passing of an object projecting out from the skin through the dressing is configured to adhere to the skin.

2. The dressing of claim 1, wherein the means for facilitating passing of an object projecting out from the skin through the dressing comprises a hole extending through the first and second film layer and the body of absorbent material disposed there between.

3. The dressing of claim 1, wherein the means for facilitating passing of an object projecting out from the skin through the dressing comprises at least two secondary slits starting in the middle of the dressing and being distanced from each other in a circumferential direction in relation to the starting point, each secondary slit ends before reaching an outer edge of the absorbent body.

4. The dressing of claim 2, further comprising at least two secondary slits that extend from the perimeter of the hole in the dressing, the secondary slits being distanced from each other in a circumferential direction, each secondary slit ends before reaching an outer edge of the absorbent body.

5. The dressing of claim 1, further comprising a primary slit that extends through the dressing from an edge thereof towards a middle portion of the absorbent body.

6. The dressing of claim 1, further comprising a stiffening layer that is releasably attached to the upper side of the dressing.

7. The dressing of claim 6, wherein the stiffening layer has the form of a frame surrounding a central portion of the dressing.

8. The dressing of claim 7, further comprising a primary slit that extends through the dressing from an edge thereof towards a middle portion of the absorbent body, wherein grip tabs extend out from the frame on both sides of the primary slit adjacent to each other.

9. The dressing of claim 7, further comprising a primary slit that extends through the dressing from an edge thereof towards a middle portion of the absorbent body, wherein the frame comprises one or more portion(s) projecting inwardly towards the middle of the absorbent body on both sides of the primary slit.

10. The dressing of claim 5, wherein the means for facilitating passing of an object projecting out from the skin through the dressing comprises a hole extending through the first and second film layer and the body of absorbent material disposed there between, wherein the first and second film layer comprises edges along the primary slit, and wherein the edges of the first and second film layer along the primary slit are attached to each other.

11. The dressing of claim 10, wherein the edges of the first and second film layer are attached to each other by a welding seam.

12. The dressing of claim 1, wherein the body of absorbent material is made of absorbent foam material.

13. The dressing of claim 4, wherein the body of absorbent material includes fibrous material disposed in a region or regions distanced from the hole and/or the secondary slits.

14. The dressing of claim 5, wherein the primary slit is discontinuous in the part thereof extended outside of the absorbent body.

15. The dressing of claim 1, wherein the soft adhesive is a soft silicone gel.

16. The dressing of claim 2, wherein a primary slit extends through the dressing from an edge thereof towards a middle portion of the absorbent body.

17. The dressing of claim 3, wherein a primary slit extends through the dressing from an edge thereof towards a middle portion of the absorbent body.

18. The dressing of claim 4, wherein a primary slit extends through the dressing from an edge thereof towards a middle portion of the absorbent body.

19. The dressing of claim 2, wherein a stiffening layer is releasably attached to the upper side of the dressing.

20. The dressing of claim 3, wherein a stiffening layer is releasably attached to the upper side of the dressing.

\* \* \* \* \*